US012558255B2

(12) United States Patent
Meier et al.

(10) Patent No.: US 12,558,255 B2
(45) Date of Patent: Feb. 24, 2026

(54) METHOD OF MANUFACTURING AN INTRAORAL DEVICE

(71) Applicant: SomnoMed Limited, Crows Nest (AU)

(72) Inventors: Joshua Luke Meier, Berowra (AU); Christopher Russell Bedford, Rozelle (AU); Wataru Obuchi, Maroubra (AU); Harrison John Wood, Ourimbah (AU); Terrence Quach, Lidcombe (AU)

(73) Assignee: SOMNOMED LIMITED, Crows Nest (AU)

( * ) Notice: Subject to any disclaimer, the term of this patent is extended or adjusted under 35 U.S.C. 154(b) by 630 days.

(21) Appl. No.: 17/595,933

(22) PCT Filed: May 29, 2020

(86) PCT No.: PCT/AU2020/050542
§ 371 (c)(1),
(2) Date: Nov. 29, 2021

(87) PCT Pub. No.: WO2020/237316
PCT Pub. Date: Dec. 3, 2020

(65) Prior Publication Data
US 2022/0226146 A1     Jul. 21, 2022

(30) Foreign Application Priority Data

May 30, 2019    (AU) ................................ 2019901867

(51) Int. Cl.
*A61F 5/56*          (2006.01)
*A61C 9/00*          (2006.01)
(Continued)

(52) U.S. Cl.
CPC ............. *A61F 5/566* (2013.01); *A61C 9/004* (2013.01); *B33Y 10/00* (2014.12); *B33Y 80/00* (2014.12)

(58) Field of Classification Search
CPC ....................................................... A61F 5/566
See application file for complete search history.

(56) References Cited

U.S. PATENT DOCUMENTS

2006/0127856 A1*  6/2006  Wen ................... A61C 13/0027
                                              433/213
2007/0183572 A1*  8/2007  Drummond ............. A61F 5/566
                                              378/98.8
(Continued)

FOREIGN PATENT DOCUMENTS

CA          3033421 A1     2/2018
WO     WO-2006096558 A2 *  9/2006   ............... A61C 7/00
(Continued)

OTHER PUBLICATIONS

International Search Report for App. No. PCT/AU2020/050542, dated Aug. 19, 2020, 10 pages.

*Primary Examiner* — Andrew D Graham
(74) *Attorney, Agent, or Firm* — Butzel Long

(57) ABSTRACT

A method of manufacturing an intraoral device (1) including: obtaining an impression of at least one row of a patient's teeth; transferring said impression into a processor; said processor communicating with a milling machine; milling a blank of a first material to form a cavity in said blank substantially corresponding to said impression, said cavity being milled to include an offset; said cavity with at least a second material and allowing said second material to cure; milling said second material to correspond to said impression; milling said first material to obtain a device shape;
(Continued)

cleaning said device (1); and wherein said first and second materials are comparatively hard and soft.

21 Claims, 6 Drawing Sheets

(51) Int. Cl.
    *B33Y 10/00*        (2015.01)
    *B33Y 80/00*        (2015.01)

(56)               References Cited

U.S. PATENT DOCUMENTS

| | | | | |
|---|---|---|---|---|
| 2015/0238289 | A1* | 8/2015 | Wouters | G05B 15/02 |
| | | | | 700/98 |
| 2015/0245890 | A1* | 9/2015 | Wouters | A61C 9/004 |
| | | | | 700/98 |
| 2017/0007442 | A1* | 1/2017 | Dietz | A61F 5/566 |
| 2017/0035533 | A1* | 2/2017 | Ross | A61C 9/0046 |
| 2017/0035534 | A1* | 2/2017 | Ross | A61F 5/56 |
| 2017/0143445 | A1* | 5/2017 | Abkai | A61F 5/566 |
| 2018/0024530 | A1* | 1/2018 | Kim | A61F 5/56 |
| | | | | 128/848 |
| 2018/0169504 | A1* | 6/2018 | Williams | A63B 71/085 |
| 2018/0193183 | A1* | 7/2018 | Kim | B23C 3/00 |
| 2018/0338856 | A1* | 11/2018 | Rago | A61F 5/08 |
| 2019/0282345 | A1 | 9/2019 | Friebauer | |

FOREIGN PATENT DOCUMENTS

| | | | |
|---|---|---|---|
| WO | 2017007962 | A1 | 1/2017 |
| WO | 2020237316 | A1 | 12/2020 |

* cited by examiner

11

20

1          11          25          22

26                    13

12                    14

26

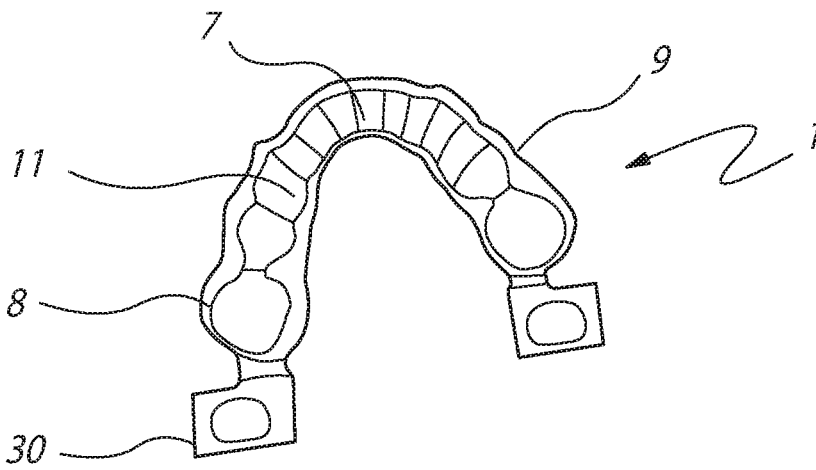
*FIG.11*
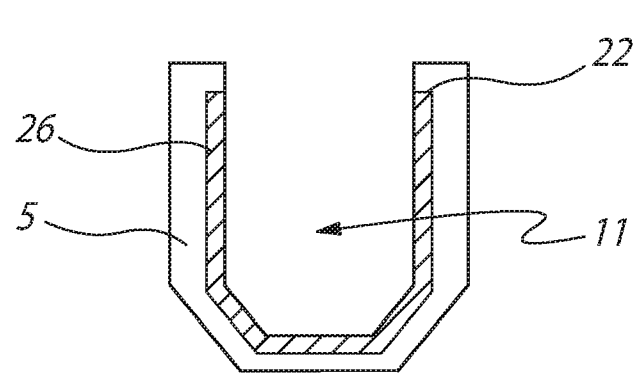
*FIG.12*
*FIG.13*

METHOD OF MANUFACTURING AN INTRAORAL DEVICE

FIELD

The present invention relates to a method of manufacturing an intraoral device, and more particularly to a multiple (i.e. at least two) material intraoral device having a soft lining.

BACKGROUND

Various forms of intraoral devices are known. One known form of an intraoral device is a mandibular advancement device that has application in the treatment of sleep disorders such as snoring or obstructive sleep apnoea (OSA), or certain temporomandibular joint disorders. Another known form of an intraoral device is a mouthguard for the protection of the teeth from impact injury (for example, a mouthguard for use during contact sports). Yet another known form of an intraoral device is a retainer or plate-type device for orthodontic applications, such as the adjustment of a patient's bite or the realignment of teeth.

The effectiveness of such devices often relies on the patient using the device as directed and the accuracy of manufacturing the device to fit the teeth and jaw of the patient. Typical known devices are made by hand and are subject to human errors and use materials that are proned to expansion and contraction problems. Such techniques include the lost wax technique, relining press technique, injection mould techniques and milling a single material. Known methods are also disadvantageous because they produce large amounts of scrap and waste.

Whilst digitally produced devices are known, they are typically formed from a single material. Such materials are typically selected for the balance of mechanical properties such as flexural strength, flexural modulus, fracture toughness and water sorption. However, they are not optimised for properties that result in higher patient comfort such as shore A hardness or elongation at break, and due to their stiffness are difficult to optimise retention (seating on the teeth), resulting in frequent device remakes.

There is a need for an intraoral device having a soft lining for patient comfort. There are handmade devices that use soft linings using the lost wax technique, thermofoil suckdown or injection system. However, the manufacturing process of these devices is not suitable with automated and digital manufacturing methods.

Accordingly, there is a need for an at least two material milled intraoral device with a soft lining. Having the soft lining milled may at least ensure dimensional precision (CNC type accuracy), resulting in an intimate and comfortable fit for the patient, while the harder base may at least provide structural integrity.

SUMMARY

It is an object of the present invention to substantially overcome, or at least ameliorate one or more of the disadvantages of existing arrangements, or at least provide a useful alternative to the existing arrangements.

There is disclosed herein a method of manufacturing an intraoral device including:

obtaining an impression of at least one row of a patient's teeth;

transferring said impression into a processor;

said processor communicating with a milling machine;

milling a blank of a first material to form a cavity in said blank substantially corresponding to said impression, said cavity being milled to include an offset;

filling said cavity with at least a second material and allowing said second material to cure;

milling said second material to correspond to said impression;

milling said first material to obtain a device shape;

cleaning said device; and wherein said first and second materials are comparatively hard and soft.

There is also disclosed herein a method of manufacturing an intraoral device including:

obtaining an impression of at least one row of a patient's teeth;

transferring said impression into a processor;

said processor communicating with a milling machine;

milling a blank of a first material to form a cavity in said blank substantially corresponding to said impression to obtain a device shape, said cavity being milled to include an offset;

filling said cavity with at least a second material and allowing said second material to cure;

milling said second material to correspond to said impression;

cleaning said device; and wherein said first and second materials are comparatively hard and soft.

There is also disclosed herein a method of manufacturing an intraoral device including:

obtaining an impression of at least one row of a patient's teeth;

transferring said impression into a processor;

said processor communicating with a milling machine;

milling a blank of a first material to form a cavity in said blank substantially corresponding to said impression, said cavity being milled to include an offset;

filling said cavity with at least a second material and allowing said second material to cure;

milling said second material to correspond to said impression;

milling said first material to obtain a device shape; and wherein said first and second materials are comparatively hard and soft.

There is disclosed herein a method of manufacturing an intraoral device including:

obtaining an impression of at least one row of a patient's teeth;

transferring said impression into a processor;

said processor communicating with a milling machine;

milling a blank of a first material to form a cavity in said blank substantially corresponding to said impression, said cavity being milled to include an offset;

filling said cavity with at least a second material;

milling said second material to correspond to said impression;

milling said first material to obtain a device shape;

cleaning said device; and wherein said first and second materials are comparatively hard and soft.

There is also disclosed herein a method of manufacturing an intraoral device including:

obtaining an impression of at least one row of a patient's teeth;

transferring said impression into a processor;

said processor communicating with a milling machine;

milling a blank of a first material to form a cavity in said
   blank substantially corresponding to said impression to
   obtain a device shape, said cavity being milled to
   include an offset;
filling said cavity with at least a second material and
   allowing said second material to cure;
milling said second material to correspond to said impres-
   sion; and wherein
said first and second materials are comparatively hard and
   soft.
There is also disclosed herein a method of manufacturing
an intraoral device including:
obtaining an impression of at least one row of a patient's
   teeth;
transferring said impression into a processor;
said processor communicating with a milling machine;
milling a blank of a first material to form a cavity in said
   blank substantially corresponding to said impression to
   obtain a device shape, said cavity being milled to
   include an offset;
filling said cavity with at least a second material;
milling said second material to correspond to said impres-
   sion;
cleaning said device; and wherein
said first and second materials are comparatively hard and
   soft.
Preferably, said offset is 0.5 mm to 1.5 mm.
Preferably, said cavity includes a base, upwardly extend-
ing side walls to a lip, said lip including a shelf.
Preferably, said first material is a relatively rigid polymer
such as acrylic, polyamide or polycarbonate.
Preferably, said second material is an elastomeric material
such as silicone, plasticized acrylic, thermoplastic polyure-
thane or vinyl copolymers.
Preferably, said second material is a heat formable mate-
rial such as polycaprolactone.
Preferably, said device is CNC milled.
Preferably, where the filling of the secondary material is
a partial filling of the cavity, to reduce material wastage.
Preferably, where the filling material is viscous, after
filling any air pockets located within said second material
shall be removed prior to curing.
Preferably where the filling material is formed by ther-
moforming.
There is disclosed herein a method of manufacturing an
intraoral device including:
obtaining an impression of at least one row of a patient's
   teeth;
transferring said impression into a processor;
said processor communicating with a 3D printing
   machine and a milling machine; 3D printing a first
   material with an offset substantially corresponding to
   said impression;
filling said cavity with at least a second material and
   allowing said second material to cure;
milling said second material to correspond to said impres-
   sion;
milling said first material to obtain a device shape;
cleaning said device; and wherein
said first and second materials are comparatively hard and
   soft.
There is disclosed herein a method of manufacturing an
intraoral device including:
obtaining an impression of at least one row of a patient's
   teeth;
transferring said impression into a processor;
said processor communicating with a milling machine;

milling a blank of a first material to form a cavity in said
   blank substantially corresponding to said impression;
forming by pressure and/or heat a foil over the cavity;
milling the cavity with an offset;
placing the foil over the blank to form a closed volume;
filling volume closed with at least a second material and
   allowing said second material to cure; and wherein
said first and second materials are comparatively hard and
   soft.
Preferably, said device is cleaned using a micromotor
tool.
Preferably device is cleaned using dry ice.
Preferably, an intraoral device is made by the method
above.
Preferably, the thickness of the first material is between
0.5 mm and 4.0 mm.
Preferably, the thickness of the second material is between
0.5 and 1.5 mm.
Preferably, the flexural modulus of the first material is
between 1000 MPa and 4000 MPa.
Preferably, the Shore A hardness of the second material is
between 55 and 99.
Preferably the device is a mouthguard.
Preferably a cutter used to mill or machine the second
material has a ball head geometry with a plurality of blades
extending radially from the ball head.

BRIEF DESCRIPTION OF THE DRAWINGS

Preferred embodiments of the invention will now be
described, by way of an example only, with reference to the
accompanying drawings, in which:
FIG. 11 shows a 3D printed version of the device of FIG.
1;
FIG. 12 shows another cross-section view of an intraoral
device;
and
FIG. 13 shows another cross-section view of an intraoral
device.

DETAILED DESCRIPTION OF THE EMBODIMENTS

One form of a known intraoral device is disclosed in
International Patent Publication No. WO 2017/106896, the
content of which is incorporated herein by reference in its
entirety. This publication relates to a form of intraoral device
known as a mandibular advancement splint (MAS) or mandibular advancement device for the treatment of snoring and obstructive sleep apnoea (OSA). This mandibular advancement device includes a lower part and an upper part, which are adapted to be fitted to the respective upper and lower jaw of a patient for use in sleep. The various parts of this mandibular advancement device are designed to advance the lower jaw of a patient in an anterior direction, thereby carrying the tongue forward and reducing the likelihood of the tongue impacting on the airway of the patient. The present invention could be used to make such a device.

Figure 2:
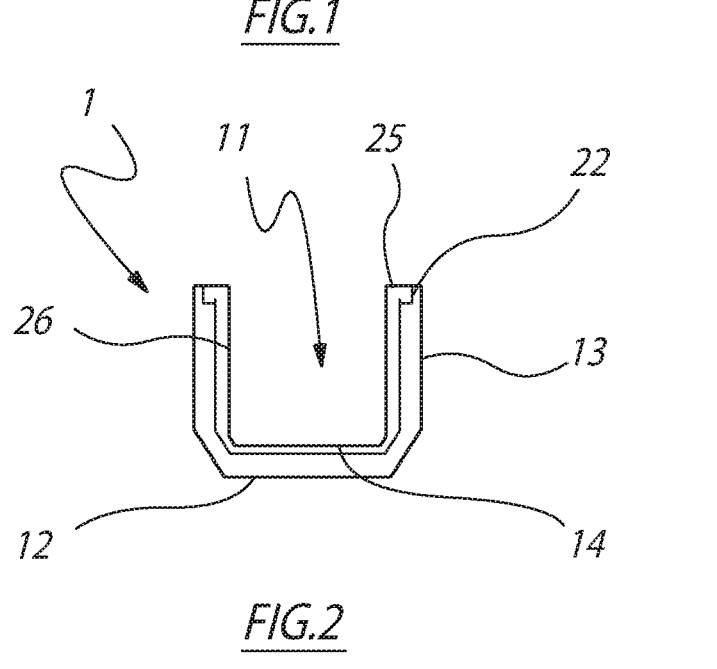
FIG. 2 shows a simple cross-section view of the final
product layers of the intraoral device of an embodiment of
the present invention.

Referring to FIGS. 2, 11, 12 and 13, for example, a typical intraoral device 1 includes a body 5 formed from a relatively rigid material such as acrylic, polyamide, polycarbonate or the like. The body 5 is adapted to be fitted in the oral cavity of a patient. The body 5 typically includes a front central portion 7 and a pair of longitudinally extending arms 8, 9. A cavity 11 extends along the central portion and arms and includes a base 12 and upwardly extending walls 13 as best seen in FIG. 2. The base 12 is adapted to be moulded to the shape of the patient's teeth.

The manufacturing of the intraoral device 1 will now be described with reference to the drawings and images.

Figure 1:
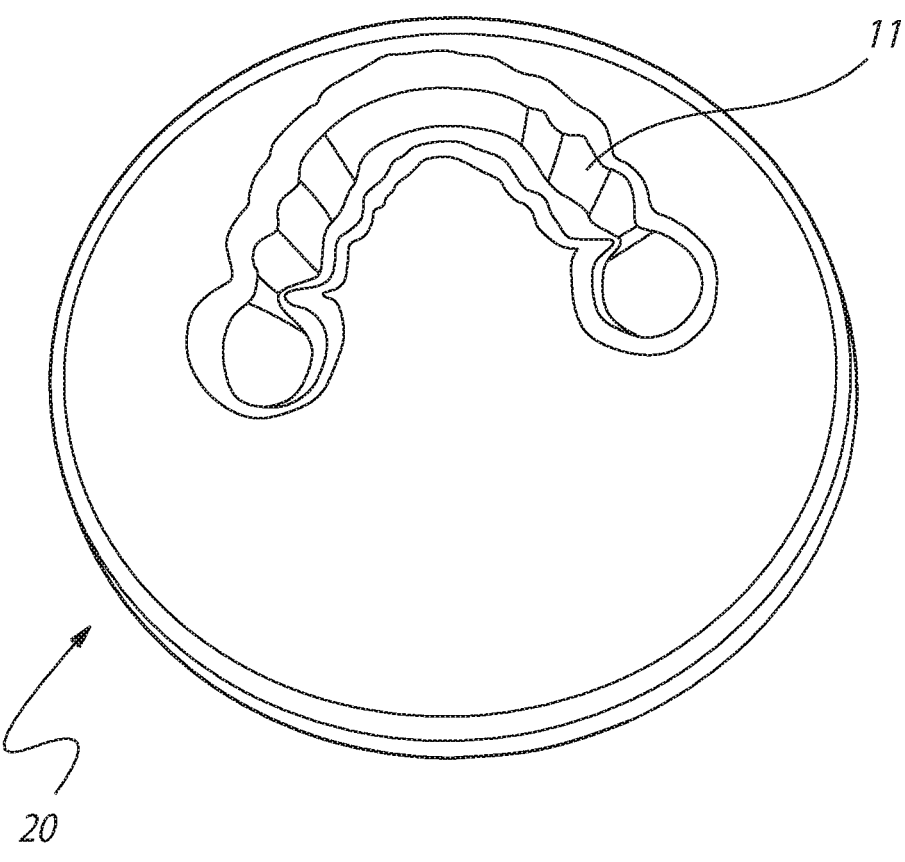
FIG. 1 shows an intraoral device blank after the first initial
milling.

An impression of a patient's teeth can be acquired from a physical record taken with polyvinyl siloxane (PVS) or similar material that is then poured up and digitised. Preferably, the physical record is acquired digitally using an intraoral scan of the teeth or a cone beam computed tomography (CBCT) scan of the teeth. For mandibular advancement splints (MAS) or devices, the dentist may use a bite gauge tool to capture a protrusive relationship. Once the impression of the patient's teeth is obtained in a digital form, the impression is uploaded to a repository of cases to be processed. The files are inspected for defects such as incomplete scan, warps or defects. Assuming that these files pass the requirements, computer-aided design (CAD) software is used to design at least two bodies, formed from a hard and a soft material. These CAD files are exported as STL or similar file type and then imported into milling software. One or more of the processors may be utilised during the process. The multiple milling stages are calculated in computer numerical control (CNC) software at a similar time, taking care to ensure that the files are not misaligned. Referring to FIG. 1, for example, the technician would take a blank 20 of suitable, preferably rigid and/or hard structural material (such as PMMA or polyamide) and mill (or otherwise remove material from the blank as shown in FIG. 1), using a milling machine, the cavity 11 in the general form of teeth. The milled cavity 11 would be offset from the accurate impression by 0.5 to 1.5 mm. This may also be known as a first general milling run.

Figure 3:
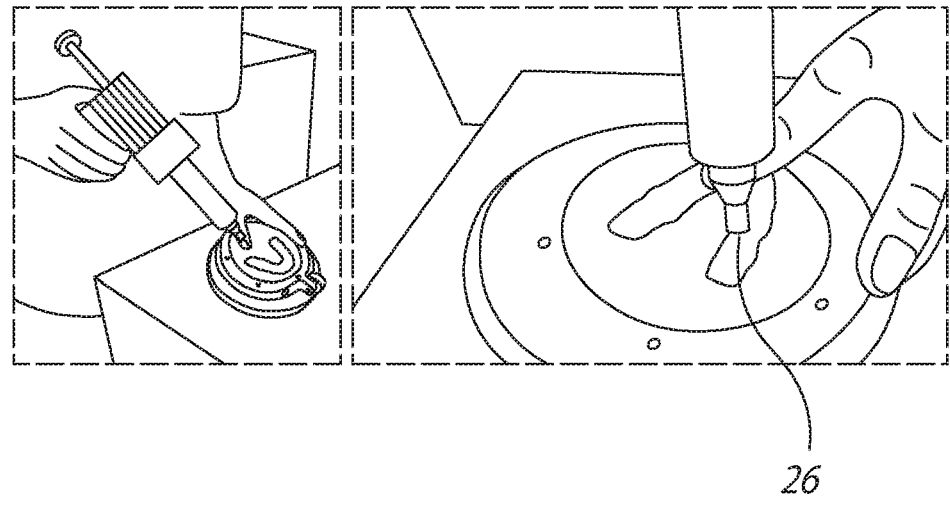
FIG. 3 shows the application of the lining material to the
blank of FIG. 1.
Figure 4:
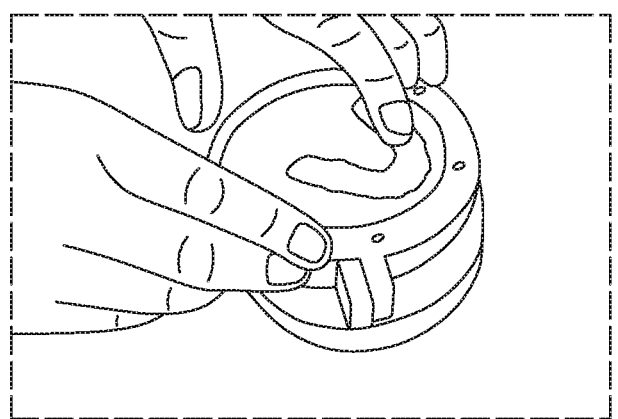
FIG. 4 shows the device of FIG. 3 manually pressed to
remove air pockets.
Figure 5:
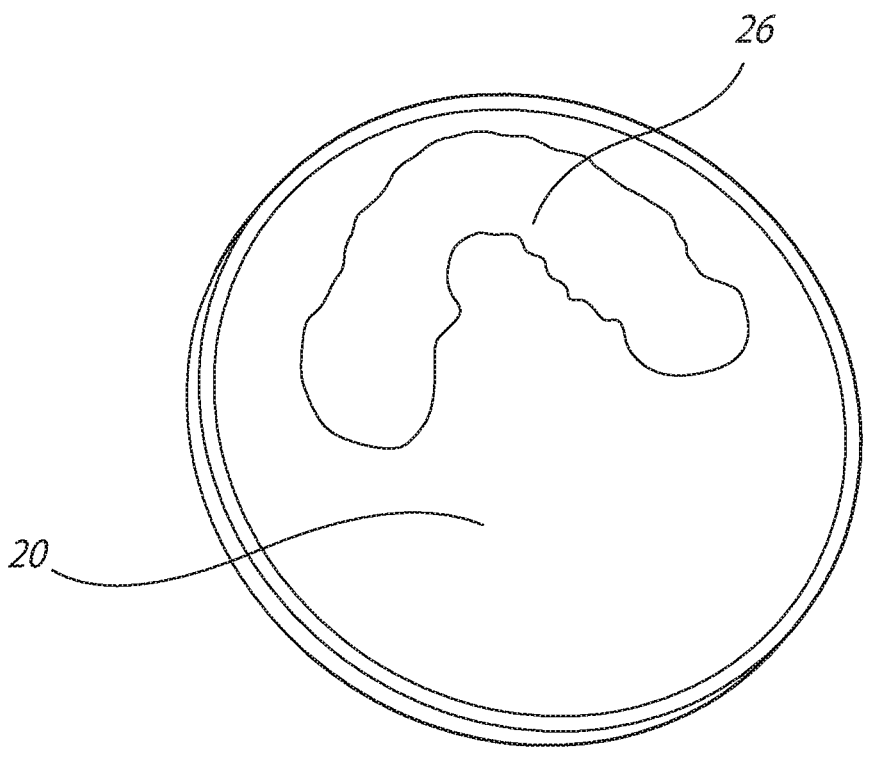
FIG. 5 shows the device of FIG. 3 filled and cured.
Figure 6:
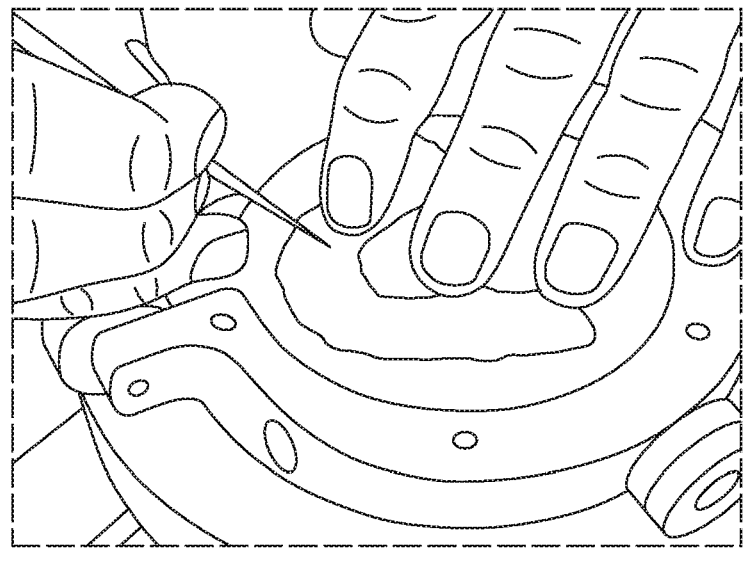
FIG. 6 shows the device of FIG. 5 with the air pockets
being lanced.
Figure 8:
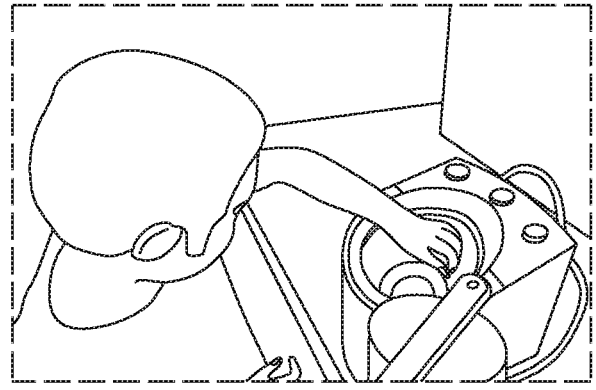
FIG. 8 shows the device of FIG. 5 being placed in a curing
flask.

As best seen in FIG. 2, the walls 13 of the cavity 11 include a shelf 22 to accommodate a flange 25 of a soft lining or insert 26. In other words, the soft lining or insert 26 is adapted to fill the cavity 11. The soft lining or insert 26 may be an elastomeric material such as silicone, plasticized acrylic, thermoplastic polyurethane, or vinyl copolymers. The soft lining or insert 26 may alternatively be a heat formable material such as polycaprolactone. It will be understood that the soft lining or insert 26 is soft relative to the material of the blank 20. The flange 25 may at least increase the surface area of the soft lining or insert 26 and mitigate failure of the bonding of the two materials 5, 26 at the junction of the soft lining 26 and the hard surface (body) 5. This arrangement may also prevent the problem of delamination during the milling process. Multiple shelves 22 forming retention grooves 40 may be present, for example, as seen in FIG. 12. The soft lining or insert 26 at the base 12 facing the cavity 11 has a fit surface 14 that is cleaned (or prepared with a primer, bond agent, plasma surface treatment, sand blasting treatment or the like) and the cavity 11 is packed completely or partially, manually or with the aid of a machine as see in FIG. 3. At this step care must be taken while applying the soft lining material 26 to remove air pockets, particularly when the soft lining material 26 is viscous to facilitate the filling of the cavity 11. If air pockets exist, they can be lanced/pierced using a probe or the like as shown in FIG. 6 providing a path for air to escape before being recompressed (FIG. 8). The soft lining or insert 26 may alternately be pressed under forces using pneumatic press, vacuum chambers or other like pressurised application methods (mechanical or hydraulic) as shown in FIGS. 4 and 8. The shelf or shelves 22 could also be milled in the reverse configuration as shown in FIG. 13.

Figure 7:
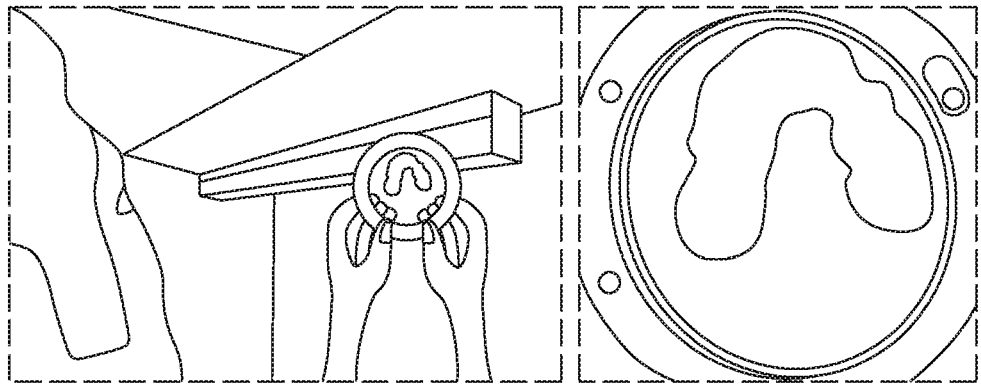
FIG. 7 shows the device of FIG. 5 being inspected for air
pockets.

As seen in FIG. 7, the filled in blank 20 can be held up to the light to check for air pockets. The filled in blank 20, along with the soft lining or insert 26, as shown in FIG. 8 is then cured at relevant processing conditions for the soft lining or insert 26. This may involve water, heat, light and/or pressure as per supplier instructions.

Figure 9:
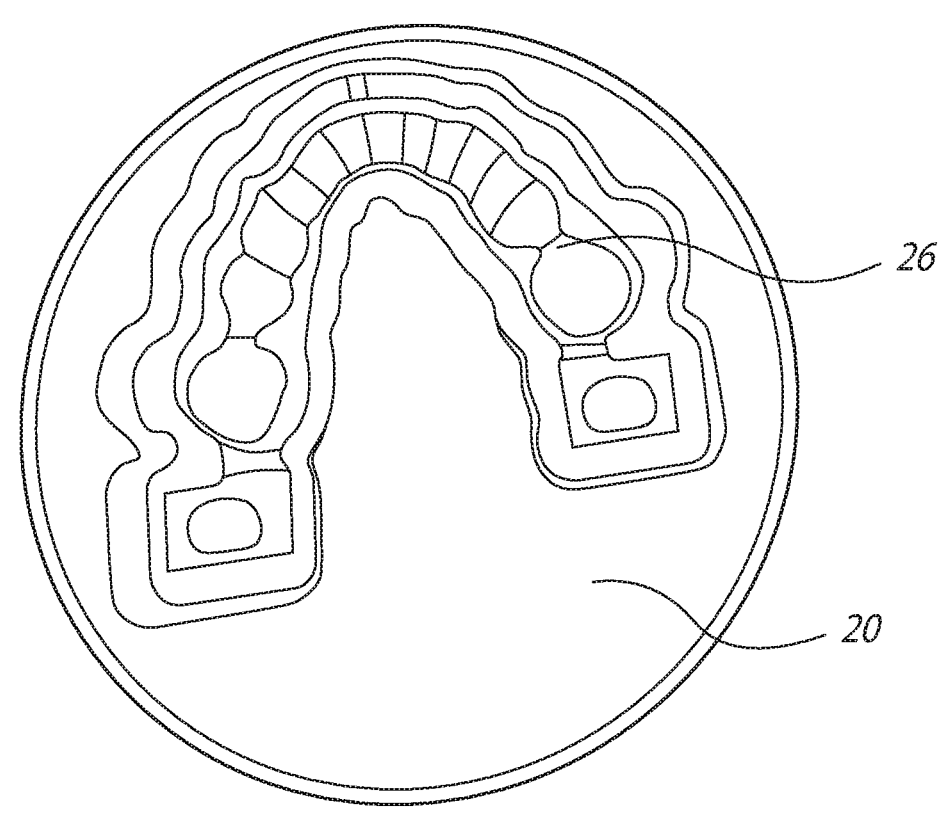
FIG. 9 shows the device of FIG. 5 after the soft lining has
been milled.

As seen in FIG. 9, the soft lining material 26 is then milled or machined to the desired dimensions of the impression using a specialised cutter. A specialised cutter would change depending upon the type of soft lining material 26 that is being utilised. The cutter may, for example, have a ball head geometry with a plurality of blades extending radially from the ball head.

Figure 10:
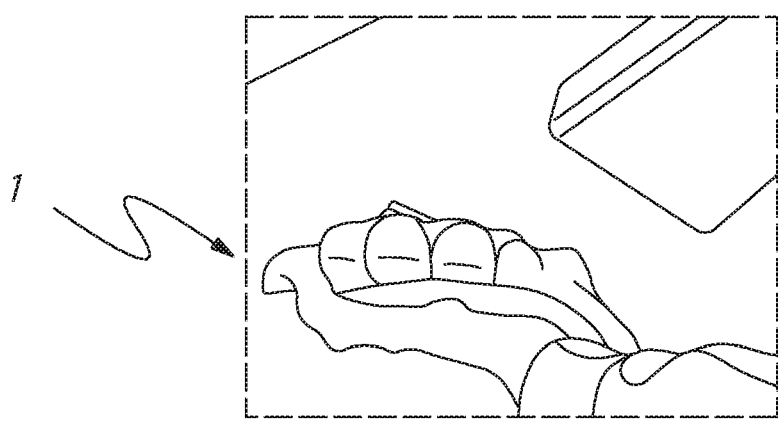
FIG. 10 shows the device of FIG. 9 after milling with burs
being removed by dry ice.

The blank 20 is then rotated and the excess hard material is removed to form the body 5, thus obtaining the shape of the device 1. Any minor burrs remaining after milling may be removed (thereby cleaning the device) using a micro motor hand piece or the like with a brush burr, or alternatively may be removed using dry ice $CO_2$ blasting or the like, as shown in FIG. 10. The blank 20 and/or the body 5 may have a thickness of between 0.5 to 4.0 mm and/or a flexural modulus of between 1000 MPa and 4000 MPa. The soft lining material 26 may have a Shore A hardness of between 55 and 99.

It will be appreciated that a method of manufacturing an intraoral device may include (and is not limited to) any one or more of the following steps:

obtaining an impression of at least one row of a patient's teeth;

transferring said impression into a processor;

said processor communicating with a milling machine;

milling a blank of a first material to form a cavity in said blank substantially corresponding to said impression, said cavity being milled to include an offset;

filling said cavity with at least a second material and allowing said second material to cure;

milling said second material to correspond to said impression;

milling said first material to obtain a device shape;

cleaning said device; and wherein said first and second materials are comparatively hard and soft.

In alternate embodiments, the full shape of the body 5 of the device 1 is obtained by milling the blank 20. The soft lining or insert 11 is then added to the cavity 11, and subsequently milled or machined to the desired impression. In further alternate embodiments, instead of using a blank and milling, the body 5 of the device 1 could be 3D printed using acrylic, polyamide, polycarbonate using technology such as FDM, SLS, DLP as generally shown. The offset of 0.5 mm to 1.5 mm may still be provided, and the 3D printer could also include a locator 30 (see FIG. 11) for assistance to the technicians. The cavity 11 could then be packed with the soft lining material 26 or sucked down. The device 1 could then follow the usual steps of the milling, locating using the fixtures 30 and mill the fit surface 14.

As mentioned above, a suckdown method could also be used using a suitable structural material such as PMMA or polyamide with an offset to accommodate the soft lining as mentioned above. In this case one or more air holes would be used at the central portion 7 and arms 8 and 9 for air to escape. A primer would then be applied along with a bonding agent then the suckdown dual laminate would occur.

The present invention at least in a preferred embodiment has significant advantages over the prior art. For example, it may at least provide comfort for the patient (soft lining plus strength) with greater compliance to the patient's teeth and fewer breakages. The method may also provide enhanced accuracy of fit, which may again lead to greater patient comfort, fewer areas of high contact pressure and more even pressure across the teeth. Due to the enhanced accuracy, there is also less tooth movement.

The method may also provide a lower risk of delamination than traditional suckdown methods due to the shelf/lip design and lancing technique, which provides a longer life device. There is a reduced need for remakes, and no physical working model is required, thus saving costs and by-products.

Alternative embodiments could include using dry ice $CO_2$ blasting to remove the burrs left on a fit surface, instead of manually doing the same with a micro motor and brush burr and also applying the technique to 3D printed parts as mentioned above. Further, the soft lining material can be deposited/dispensed by CNC robotic dispensing systems, thus providing less waste instead of packing the cavity with greater control dispensing amount of material required on marginally more than required. Greater control equals fewer errors as the process is automated, and new materials may also become available for use, instead of only acrylic or polyamide. Plasma surface treatment or sand blasting may also improve the soft lining bond strength. The milling of the soft lining material is particularly advantageous.

Accordingly, the present invention at least in the preferred embodiment may at least provide an extremely precise fitting of a dual material device fabricated digitally and automatically. The arrangement may at least remove most (if not all) human errors and remove inherent errors from the expansion and contraction of materials which are characteristics of traditional processes. The highly desirable characteristics of dual laminate materials may at least provide a balance of flexibility and comfort including strength and durability. The device could, in a preferred form, be a sleep apnea device. However, the device could also be a bruxism splint, mouthguard, denture, hearing aid or the like.

Although the invention has been described with reference to preferred embodiments, it will be appreciated by those persons skilled in the art that the invention may be embodied in many other forms.

The invention claimed is:

1. A method of manufacturing an intraoral device including:
    receiving an impression of at least one row of a patient's teeth;
    forming, in a first material, a cavity substantially corresponding to said impression, said cavity having an offset from said impression;
    filling said cavity with at least a second material;

curing said second material within said cavity by placing the intraoral device in a curing flask and applying at least one of water, heat, light, and pressure to cure the first material and the second material;
    milling said second material to correspond to said impression; and
    milling said first material to obtain a shape of the intraoral device;
    wherein said first material is comparatively harder than said second material.

2. The method of claim 1, wherein the forming the cavity comprises:
    milling a blank of said first material to form the cavity in said blank; or
    3D printing the first material with the cavity formed in said first material.

3. The method of claim 1, further including:
    forming by pressure and/or heat a foil over the cavity;
    placing the foil over a blank to form a closed volume; and
    filling the closed volume with said second material.

4. The method of claim 1, wherein said offset is 0.5 mm to 1.5 mm.

5. The method of claim 1, wherein said first material is a rigid polymer, wherein the rigid polymer is any one of acrylic, polyamide, and polycarbonate.

6. The method of claim 1, further including cleaning said device.

7. The method of claim 1, further including sandblasting a surface of said cavity.

8. The method of claim 1, further including applying a primer or bonding agent to a surface of said cavity.

9. The method of claim 1, wherein said second material is an elastomeric material or a heat formable material.

10. The method of claim 1, wherein said milling is performed by computer numerical control software.

11. The method of claim 1, wherein the filling of the second material is a partial filling of the cavity, to reduce material wastage.

12. The method of claim 1, wherein the second material is viscous, the method further including:
    removing, after filling and prior to curing, any air pockets located within said second material.

13. The method of claim 1, wherein the second material is formed by thermoforming.

14. The method of claim 6, wherein said device is cleaned using a micromotor tool or dry ice.

15. The method of claim 1, wherein the thickness of the first material is between 0.5 mm and 4.0 mm.

16. The method of claim 1, wherein the thickness of the second material is between 0.5 and 1.5 mm.

17. The method of claim 1, wherein the flexural modulus of the first material is between 1000 MPa and 4000 MPa.

18. The method of claim 1, wherein the Shore A hardness of the second material is between 55 and 99.

19. The method of claim 1, where a cutter used to mill or machine the second material has a ball head geometry with a plurality of blades radially extending from the ball.

20. A method of manufacturing an intraoral device including:
    receiving an impression of at least one row of a patient's teeth;
    forming, in a first material, a channel defining a cavity substantially corresponding to said impression, said cavity having an offset from said impression, wherein the channel includes a pair of upwardly extending side walls and a base, wherein each upwardly extending side wall is coupled to the base at a proximal end of the upwardly extending side wall, wherein each upwardly extending side wall includes a protrusion and a plurality of retention grooves, wherein the protrusion extends from a distal end of the upwardly extending side wall, the plurality of retention grooves being arranged along the upwardly extending side wall between the protrusion and the proximal end;

filling said cavity with at least a second material, wherein the first material and the second material are cured together by applying at least one of water, heat, light and pressure when the second material is within said cavity;

milling said second material to correspond to said impression; and milling said first material to obtain a shape of the intraoral device;

wherein said first material is comparatively harder than said second material.

21. An intraoral device for receiving patient's teeth, the intraoral device including:

a body formed in a first material; and a lining formed in a second material, wherein the first material is comparatively harder than the second material;

the body including a channel defining a cavity substantially corresponding to an impression of a row of the patient's teeth, the cavity having an offset from the impression to accommodate the lining;

wherein the channel includes a pair of upwardly extending side walls and a base, wherein each upwardly extending side wall is coupled to the base at a proximal end of the upwardly extending side wall, wherein each upwardly extending side wall includes a protrusion and a plurality of retention grooves, wherein the protrusion extends from a distal end of the upwardly extending side wall, the plurality of retention grooves being arranged along the upwardly extending side wall between the protrusion and the proximal end;

wherein the cavity is configured to be filled with the second material, wherein the second material fills the plurality of retention grooves such that the lining is substantially levelled with the protrusions of the upwardly extending side walls; and wherein the first material and the second material are cured together by applying at least one of water, heat, light and pressure when the second material is within said cavity wherein the second material is configured to be milled after curing to form the lining corresponding to the impression.

* * * * *